United States Patent [19]

Shattuck

[11] Patent Number: 5,411,484

[45] Date of Patent: May 2, 1995

[54] BIOMEDICAL TUBE HOLDING DEVICE

[76] Inventor: Bruce T. Shattuck, P.O. Box 63477, Pipe Creek, Tex. 78063-3477

[21] Appl. No.: 132,054

[22] Filed: Oct. 5, 1993

[51] Int. Cl.$^6$ .............................................. A61M 25/02
[52] U.S. Cl. .............................. 604/179; 128/DIG. 26
[58] Field of Search ..................... 604/174, 179, 180; 128/DIG. 6, DIG 26

[56] References Cited

U.S. PATENT DOCUMENTS

| 3,430,300 | 3/1969 | Doan | 604/180 |
|---|---|---|---|
| 4,088,136 | 5/1978 | Hasslinger et al. | 604/179 |
| 4,142,527 | 3/1979 | Garcia | 128/DIG 26 |
| 4,333,468 | 6/1982 | Geist | 604/180 |
| 4,447,238 | 5/1984 | Eldridge, Jr. | 128/DIG. 26 |
| 4,548,200 | 10/1985 | Wapner | 604/179 |
| 4,617,017 | 10/1986 | Hubbard et al. | 128/DIG. 26 |
| 4,622,034 | 11/1986 | Shattuck | 604/179 |
| 4,632,670 | 12/1986 | Mueller, Jr. | 128/DIG. 26 |
| 4,700,432 | 10/1987 | Fennell | 604/179 |
| 4,844,061 | 7/1989 | Carroll | 604/179 |
| 5,019,050 | 5/1991 | Lynn et al. | 128/DIG. 26 |

Primary Examiner—Paul J. Hirsch
Attorney, Agent, or Firm—Gunn, Lee & Miller

[57] ABSTRACT

A biomedical tube stabilizing device comprised of a soft cincture made of a resilient, sterilizable material having a permanently formed loop for receiving a biomedical tube such as a tracheal or esophageal tube at one end. Following intubation, the loop is placed over the exposed portion of the biomedical tube, and the free end encircles the head and is wrapped around the biomedical tube. The tube is secured by pulling the free end in opposition to the loop engaging the biomedical tube and attaching it to the body of the encircling cincture with a tab of Velcro-like material. An alternative embodiment calls for the biomedical tube receiving loop to be formed by releasably attaching one end of the cincture to itself with a tab of Velcro-like material. An additional embodiment applies a treatment to the inner surface of the biomedical tube receiving loop in order to increase grip strength.

2 Claims, 2 Drawing Sheets

BIOMEDICAL TUBE HOLDING DEVICE

BACKGROUND OF THE INVENTION

The present invention relates to a disposable cincture and a method for stabilizing, securing and otherwise holding biomedical tubing such as endo-, naso-tracheal, and esophageal tubes, and the like.

Traditionally when patients, who require ventilatory support or gastro-intestinal intervention are intubated with a tracheal or esophogeal tube, either orally or nasally, the tube is secured or stabilized to prevent accidental extubation by taping it to the patient's face with adhesive tape. Alternatively, currently available commercial tube holders, most of which use straps, adhesives, or a combination thereof, are used to anchor the tubes to the patient's face.

Most biomedical tube holding devices are either cumbersome, restricted to holding a specific or narrow range of tube types, rely heavily on adhesives, or are uncomfortable and often expensive.

Reliable methods of securing biomedical tubes are of critical importance to patient safety particularly with the use of endotracheal tubes. Intra-operatively, endotracheal tubes are used to provide ventilatory support for patients undergoing surgery under general anesthesia. Since the patients cannot breath for themselves, a dislodged endotracheal tube would interfere with ventilation resulting in death or severe brain injury due to a lack of oxygen. In emergency medical service, where patients may require ventilatory support following trauma, poisoning, drowning, etc., survival depends on a reliably secure airway. These patients can be conscious, and are often combative, requiring the endotracheal tube stabilizing device to be all the more reliable. Moisture accumulation from exhaled air, saliva and other secretions can quickly saturate the endotracheal securing means causing the potential for slippage and subsequent dislodging of the endotracheal tube.

Currently, the preferred method of securing biomedical tubes, such as the endotracheal tube, is to circumferentially wrap adhesive tape around the exposed portion of the tube followed by attachment of the tape to the facial area surrounding the insertion point. While this approach provides a reasonably reliable means for securing the endotracheal tube, it is not without significant drawbacks. Health care providers, as a general rule, have begun wearing latex or plastic examination gloves in order to minimize the potential for coming in contact with bacterial and viral agents that can be life threatening. The smooth uniform surface of latex and plastic examination gloves provides a surface to which adhesive tape sticks tenaciously, often causing the gloves to tear while attempting to disengage from the tape. Additionally, this adhesive tenacity can cause great difficulty in handling and applying the tape when wearing plastic or latex gloves such that the process of securing the endotracheal tube can be prolonged or altogether confounded. The presence of facial hair, such as beards and/or moustaches, makes securing the endotracheal tube almost impossible.

Currently available commercial alternatives are themselves not without significant drawbacks. A device described by Wapner U.S. Pat. No. 4,548,200 comprised of a short strip of Velcro type material having a dense array of hooks and an adhesive back is circumferentially wrapped around the exposed portion of the endotracheal tube. A band of soft material having a dense array of loops for engaging the Velcro hooks is wrapped around the Velcro adhering to the tube, with the opposing ends encircling the head. Velcro tabs with hooks attach the ends to the encircling portions of the bands after criss-crossing behind the head. While initially providing secure fixation of the endotracheal tube, accumulating moisture neutralizes the adhesion between the tube and circumferentially attached Velcro hook strip as well as saturating the soft band. Because the Velcro strip is no longer held securely, and adhesion to the tube is lost, the Velcro strip often slips down into the patient's mouth posing both the threat of extubation and ingestion or inhalation of a foriegn body. Other shortcomings of this device are that the patient's head must be lifted in order to encircle and secure the bands. The tab of Velcro hooks which are affixed to the tube can also obscure depth gradations making assesement of proper tube position difficult. Application of the adhesive backed tab of Velcro hooks while wearing protective gloves can be plagued by the same problems as experienced with tape.

Another device, identified as the "Tube Restraint", which has avoided the use of adhesives is that disclosed by Shattuck (U.S. Pat. No. 4,622,034). This device consists of two flexible strips, one of resilient polyester foam and the other of nylon tricot having a porous side and a smooth side, laminated into a single piece. At one end of the strip is a 2¾ inch slit and at the opposite end is a tab of Velcro hooks. Since the slit evolves from dividing the strip longitudinally into two sections, the tensile strength of the resulting sections is reduced by half and may, therefore, be subject to failure under extreme stress such as can be imposed by combative patients struggling to dislodge the endotracheal tube from their trachea. Further, by dividing the foam strip into two portions the narrower sections become more susceptible to stretching and absorption of saliva resulting in a diminution of the grip on the tube.

Carrol discloses yet another variation on this art, (U.S. Pat. No. 4,844,061). An adhesive strip permanently affixed to the end of an elongated strip similar to that disclosed by Shattuck is circumferentially adhered to a portion of the endotracheal tube protruding from the mouth of a patient. The opposing end encircles the head, and is wrapped around the tube attaching to the encircling band by a tab of Velcro hooks. This embodiment suffers from the same drawbacks as the devices disclosed by Wapner and Shattuck, in that moisture from saliva can neutralize the adhesion between tube and the adhesive strip, the adhesive strip can stick to protective gloves, and the tensile strength of the adhesive strip may be insufficient to adequately tighten the elongated strap so as to create a reliably secure fixation of the tube.

Health care providers require that biomedical tube holders reliably fixate biomedical tubes without the use of adhesives, can be applied quickly and simply, are disposable, comfortable for the patient, and are available at the lowest possible cost.

The purpose of the Biomedical Tube Holding device is to safely, securely, and reliably secure or fixate a biomedical tube. It is the intent and object of the Biomedical Tube Holding device to provide a holder that does not use skin adhering adhesives or foam strips with slits that may weaken and tear apart under extreme stress and cause the tube to dislodge. It is a further object of this invention to accommodate patients of any size, with comfort. In addition, the device is removable, re-applicable, sterilizable, and disposable.

SUMMARY OF THE INVENTION

The Biomedical Tube Holding Device is a soft cincture made of a sterlizable material such as tricot having a dense array of loops disposed about both surfaces for releasably engaging Velcro type hooks. At one end, a loop is formed by folding the cincture onto itself and permanently attaching the end to the body of the cincture, or releasably attaching the end with a Velcro-like tab. The loop is sufficiently large in diameter so as to easily accommodate and encompass a medical tube, such as an endotracheal or endoesophogeal tube. The other end of the cincture encircles the head and is wrapped around the biomedical tube. The tube is secured by pulling the free end in opposition to the looped end and releasably fastening it to the encircling band with another Velcro-like tab. This Velcro-like tab is releasably attached to the free end of the cincture so that it can be reused should trimming of the cincture be necessary. The broad inner surface of the loop provides ample gripping capability to securely hold the tube even after saturation with moisture. tensile strength to resist stretching and tearing.

BRIEF DESCRIPTION OF THE DRAWINGS

The attributes and benefits of the presently disclosed invention can be better understood by referring to the appended illustrations and their associated descriptions.

The appended illustrations provide only the preferred embodiments of this invention, and therefore should not be considered as limiting the scope of the disclosure. While this disclosure admits to a preferred embodiment, the present invention may also address other equally effective embodiments.

DETAILED DESCRIPTION OF THE PREFERRED EMBODIMENTS

Figure 1:
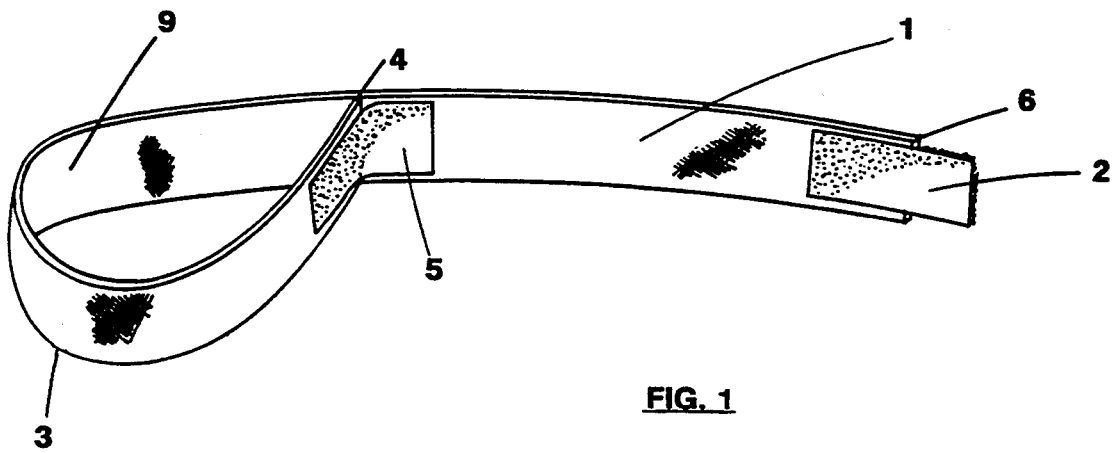
FIG. 1 is a perspective view of the biomedical tube stabilizing cincture having a permanently formed loop at one end, and a free end to which is attached a Velcro-like, releasable fastening tab containing a dense array of hooks.
Figure 2:
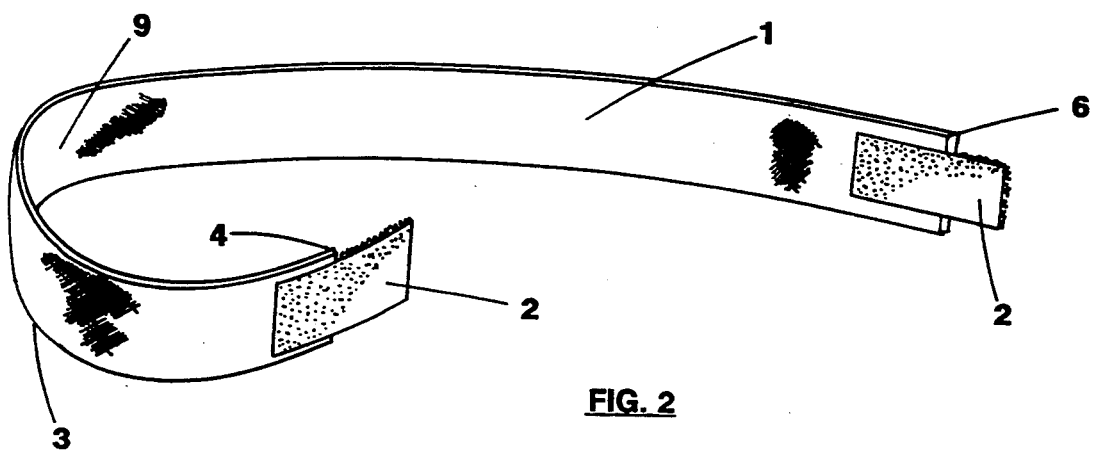
FIG. 2 is a perspective view of the biomedical tube stabilizing cincture having two free ends to which are attached Velcro-like, releasable fastening tabs containing dense arrays of hooks.
Figure 3:
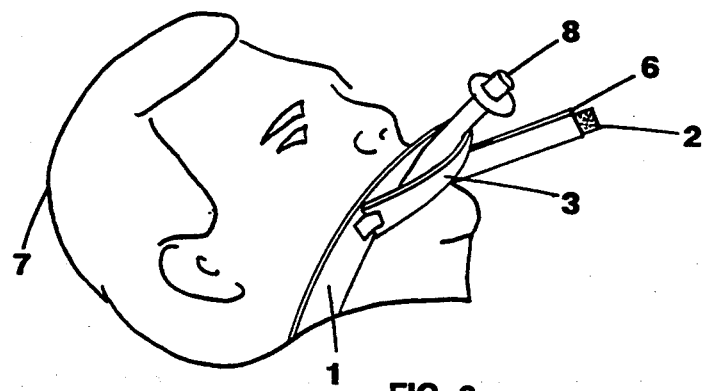
FIGS. 3—5 are side perspective views showing the method used for applying and securing biomedical tubes such as a tracheal or esophageal tube.
Figure 4:
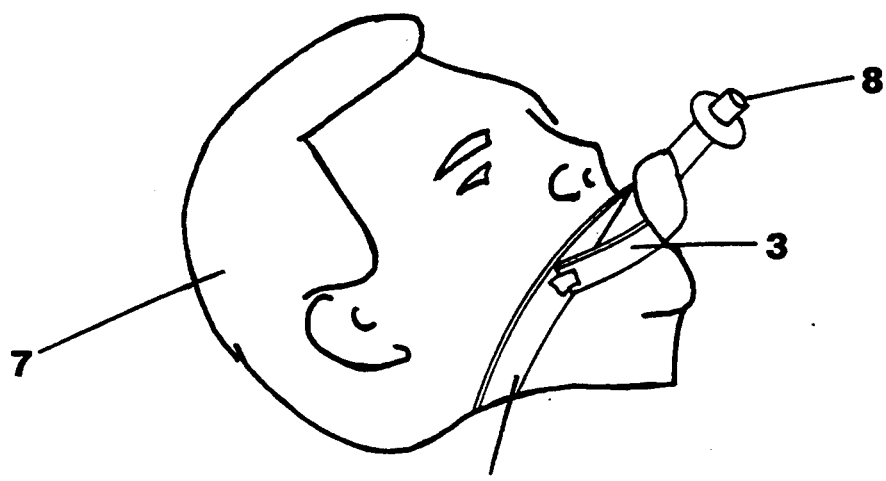
Figure 5:
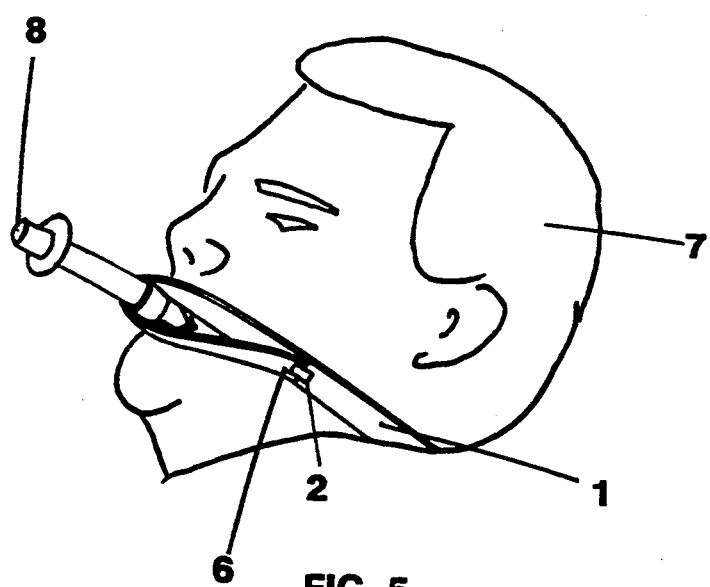

Referring to the appended illustrations, FIG. 1 is a perspective view of an embodiment of the present invention for securing or otherwise stabilizing a biomedical tube. The device is a cincture 1 made of a soft resilient, sterilizable material, such as tricot, having a dense array of loops disposed about both surfaces. At one end is a loop 3 formed by folding the cincture 1 onto itself and permanently attaching the end 4 to the body of cincture 1. A permanent attachment can be formed by a means producing a strong reliable union such as heat sealing a tab 5 to the end 4 and body of cincture 1. Loop 3 is sufficiently large in diameter so as to easily accommodate and encompass a medical tube, such as an endotracheal or endoesophogeal tube. A Velcro-like tab 2 having a dense array of hooks is releasably attached to end 6. FIG. 2 shows an alternative embodiment in which a loop 3 can be formed by folding the cincture i onto itself and attaching end 4 to the body of cincture 1 using a Velcro-like tab 2 having a dense array of hooks for engaging the loops disposed on the surface of cincture 1. As in FIG. 1, a Velcro-like tab 2 having a dense array of hooks is releasably attached to end 6. The inner surface 9 of loop 3 may be optionally treated with a non-slip material in order to further facilitate grip strength. Following intubation of a patient 7 as depicted in FIG. 3, loop 3 of the biomedical tube stabilizing device is placed over the exposed portion of the endotracheal or endoesophogeal tube 8. The free end 6 of cincture 1 encircles the patient's head 7, and is wrapped around the biomedical tube 8 as shown in FIG. 4. In FIG. 5 the tube 8 is secured by pulling end 6 of cincture 1 in opposition to the loop 3 and fastening end 6 to the encircling cincture X with a Velcro-like tab 2. Alternatively, the free end of cincture 1 can be trimmed prior to attachment with the Velcro-like tab 2 which is releasably attached to end 6 so that it can be removed prior to trimming and reattached as previously described.

With regard to the description of this invention, additional modifications and alternative embodiments may become obvious to practitioners of the art. It should therefore be understood, that the presentation of the details of this invention are for informational purposes only so that anyone skilled in the art can execute this invention. It should further be recognized that the disclosure herein presented represents the currently preferred embodiments and that additional changes in shape, size, material and methods of construction, may be made. For example, in order to facilitate securing pediatric biomedical tubes, it may be necessary to reduce in size any or all dimensions and/or specify equivalent materials, designs, and/or methods associated with the herein disclosed device design.

What is claimed:

1. A method for stabilizing an endo-tracheal or naso-tracheal tube following tracheal intubation of a patient, which comprises steps of:

stretching a tracheal securing device across a flat surface such as an operating table or an ICU bed such that the body of a cincture is underneath and oriented perpendicular to the patient's neck, said tracheal securing device including;

a noose for encircling the endo-tracheal or naso-tracheal tube permanently formed at one end of a length of cincture made of resilient, sterilizable material, such as Tricot, having a dense array of loops disposed about its surfaces;

means for releasably attaching the free end of said cincture to itself, such as a tab of material containing a dense array of hooks about the surfaces of the cincture for engaging said loops;

placing the noose of said tracheal securing device over the shaft of said endo-tracheal or naso-tracheal tube and sliding said noose down said shaft so as to be level with an oral or nasal opening where said endo-tracheal or naso-tracheal tube is located;

pulling the free end of said tracheal securing device taut such that a portion of said noose directly engages said endo-tracheal or naso-tracheal tube, wrapping said free end tightly around the said endo-tracheal or naso-tracheal tube to apply frictional force circumferentially to the endo-tracheal or naso-tracheal tube, thus preventing tube slippage;

releasably attaching the free end of said cincture by maintaining the tautness of the free end and engaging a said array of hooks to the body of said cincture in an area toward an ear of said patient to apply bi-directional force restricting lateral motion of said endo-tracheal or naso-tracheal tube.

2. The method for stabilizing an endo-tracheal or naso-tracheal tube following tracheal intubation of a patient as recited in claim 1 wherein said noose directly engages said endo-tracheal or naso-tracheal tube, such that said noose easily slips over said endo-tracheal or naso-tracheal tube.

* * * * *